United States Patent [19]
Berneman et al.

[11] Patent Number: 5,807,744
[45] Date of Patent: Sep. 15, 1998

[54] USE OF INTERFERON γ FOR THE INHIBITION OF PROLIFERATION AND DIFFERENTIATION OF PRIMITIVE HEMATOPOIETIC PROGENITOR CELLS

[75] Inventors: Zwi Berneman, Antwerp; Dirk Van Bockstaele, Edegem; Hans-Willem Snoeck, Antwerp, all of Belgium

[73] Assignee: Boehringer Mannheim GmbH, Mannheim, Germany

[21] Appl. No.: 514,897

[22] Filed: Aug. 14, 1995

[30] Foreign Application Priority Data

Aug. 13, 1994  [EP]  European Pat. Off. ........... 94112688.0

[51] Int. Cl.$^6$ .................................................. G01N 33/374
[52] U.S. Cl. ...................... 435/372; 435/372.2; 435/375; 435/377; 435/384; 435/385; 435/386; 435/811
[58] Field of Search .................................. 435/372, 372.2, 435/375, 377, 384, 385, 386, 811

[56] References Cited

U.S. PATENT DOCUMENTS 4,714,680  12/1987  Civin .

FOREIGN PATENT DOCUMENTS

PCT/US90/05451  4/1991  WIPO .

OTHER PUBLICATIONS

Alföldi, L., et al., "Induction of interferon and radioprotective activity of polyriboguanylic–polyribocytidylic acid complex in mice", *Acta microbiol. Acad. Sci. hung.*, 26:213–216 (1979).

Brugger, W., et al., "Ex vivo Expansion of Enriched Peripheral Blood CD34$^+$ Progenitor Cells by Stem Cell Factor, Interleukin–1β. (IL–1β), IL–3, Interferon–γ, and Erythropoietin", *Blood*, 81(10):2579–2584 (1993).

Richman, C.M., et al., "Interferon Protects Normal Human Granulocyte/Macrophage Colony–Forming Cells from Ara–C Cytotoxicity", *Journal of Biological Response Modifiers*, 9:570–575 (1990).

Rowley, S.D., and Davis, J.M., "Purging Techniques in Autologous Transplantation", *Bone Marrow and Stem Cell Processing: A Manual of Current Techniques*, Areman, E.M., Deeg, H.J., and Sacher, R.A. (eds.), F.A. Davis Co., Philadelphia, Pennsylvania, USA: 218–235 (1992).

Snoeck, H., et al., "Interferon–gamma and interleukin–4 reciprocally regulate the production of monocytes/macrophages and neutrophils through a direct effect on committed monopotential bone marrow progenitor cells", *European Journal of Immunology*, 23:1072–1077 (1993).

Snoeck, H., et al., "Differential regulation of the expression of CD38 and human leukocyte antigen–DR on CD34+ hematopoeitic progenitor cells by interleukin–4 and interferon–gamma", *Experimental Hematology*, 21(11):1480–1486 (1993).

Snoeck, H., et al., "Interferon–gamma is a specific inhibitor of very primitive CD34+CD38–human hematopoietic progenitor cells and not of more mature CD34+CD38+ progenitor cells", *Journal of Cellular Biochemistry Supplement*, 18A:15, (1994).

Snoeck, H., et al., "Regulation of myelopoiesis by interferon–gamma (IFN–gamma) and interleukin–4 (IL–4)", *British Journal of Haematology*, 87(1):107 (1994).

Snoeck, H.W., et al., "Interferon gamma selectively inhibits very primitive CD34++CD38–and not more mature CD34+ CD38+ human hematopoietic progenitor cells", *The Journal of Experimental Medicine*, 180:1177–1182 (1994).

*Primary Examiner*—Laurie Scheiner
*Attorney, Agent, or Firm*—Nikaido Marmelstein Murray & Oram LLP

[57] ABSTRACT

The invention provides a method for inhibition of proliferation of primitive hematopoietic progenitor cells and hematopoietic stem cells, by incubating preparations containing said cells with IFN-γ. The method is especially useful for protecting said cells during purging techniques using cytotoxic treatment, and for protection of said cells during in vivo cytotoxic treatment.

15 Claims, 2 Drawing Sheets

USE OF INTERFERON γ FOR THE INHIBITION OF PROLIFERATION AND DIFFERENTIATION OF PRIMITIVE HEMATOPOIETIC PROGENITOR CELLS

BACKGROUND OF THE INVENTION

The invention concerns the use of interferon γ for the inhibition of proliferation and differentiation of primitive hematopoietic progenitor cells and hematopoietic stem cells and its use in the in vivo and in vitro protection of said cells against cytotoxic treatment.

Many cancer patients receive intensive chemo- and/or radiotherapy to eradicate their tumour cells. This consists of several courses of chemotherapeutics, belonging to different classes, or irradiation. These courses put a high strain on the patient's bone marrow cells: cycling bone marrow progenitors can be damaged and the primitive hematopoietic progenitor cells and hematopoietic stem cells will experience a high differentiative stress with the ultimate risk of exhaustion of said cells. Protective measures are thus warranted in order to rescue the patient's bone marrow and/or to intensify the chemo- or radiotherapy.

Autologous transplantation of bone marrow plays an important role to rescue patients from intensive chemo-/radiotherapy for, e.g., certain acute leukemias, Hodgkin's and non-Hodgkin's lymphomas, multiple myeloma and selected solid tumors. Promising experimental work is currently being done in the areas of transplantation of cultured autologous bone marrow for chronic myelogenous leukemia, transplantation of purified hematopoietic stem cells, transplantation of umbilical cord blood and gene replacement therapy using genetically engineered hematopoietic stem cells. All of these uses for bone marrow transplantation bring with them the requirement for specific treatment of the marrow before it can be infused in the recipient.

The reason is that even when patients are in complete clinical remission some workers have been able to culture clonogenic tumor cells from the marrow. As relapse is in some cases induced by the contaminating tumor cells reinfused with the marrow it is logical to attempt to remove these cells prior to marrow infusion. This technique is called "purging". Purging must be done, of course, without injuring the hematopoietic progenitor cells. Many techniques have been developed for in vitro purging of occult clonogenic tumor cells from harvested autologous bone marrow. They can be broadly categorized as immunologic and non-immunologic procedures (Areman et al. (51)).

In non-immunologic methods, cytotoxic agents have been used as means of eradicating clonogenic leukemic cells while sparing uncommitted hematopoietic progenitor cells. Derivatives of cyclophosphamide, such as 4-hydroperoxycyclophosphamide, ASTA-Z (mafosphamide), as well as other chemotherapeutic drugs have been widely used. Purging is performed by incubating in the marrow generally a purified mononuclear cell suspension with the drug for the appropriate time period after which the marrow is washed and cryopreserved.

Radioisotopes, photoactivated dyes and irradiation are also used.

However, such substances and irradiation also injure to some extent the bone marrow cells. Therefore, there exists a need for a method for protection of stem cells during the purging procedures in vitro and/or during in vivo chemotherapy administration for cancer therapy. Several ways of acquiring hematoprotection have been put forward in the past. Two main explorative ways have been investigated.

A first way is through using chemical modifiers to modify the state of tumor cells or normal tissue in order to achieve therapeutic gain. Most of these are based on the anti-oxidant properties of the agents so as to remove or detoxify the reactive oxygen species and their products formed by the action of ionizing radiation or alkylating agent chemotherapy.

Within this group one can distinguish
1) a number of sulfhydryl containing compounds with free radical scavenging properties, such as
   a) the amino acid cysteine and acetylcysteine (Selig et al. (1))
   b) thiols, such as
      b1) cysteamine (Vacek et al. (2))
      b2) WR2721 (=amifostine=ethiofos)=5-2-(3-aminopropylamino)ethyl-phosphorothioic acid (Capizzi et al. (4))
      b3) DDTC=diethyldithiocarbamate (Hanson and Ainsworth (5))

A combination of this type of compounds with non-steroidal antiinflammatory drugs such as the cyclooxygenase inhibitor indomethacin (Hanson and Ainsworth (5)) or diclofenac (Kozubik et al. (3)) have been described. Rationale behind this, is the fact that these drugs inhibit prostaglandin synthesis (Hanson and Ainsworth (5)). Prostaglandin is known to be a negative regulator of colony stimulating factors (CSF) synthesis, and as such these drugs increase the proliferation of surviving hematopoietic cells.

2) The eicosanoids which are biological active compounds derived from arachidonic acid. The mechanism of protection is probably due (in part) to hypoxia (Walden (6)). Of these compounds, leukotriene appears to be the most protective.
3) Lipoic acid, a lipophilic antioxidant, has also been reported to be radioprotective (Ramakrishnan et al. (7)).
4) Calcium antagonists have also been reported to protect mice against lethal doses of ionizing radiation (Floersheim (8)). Protection may be due to interference with the damaging cellular influx of calcium after radiation-induced free radicals or by their direct inactivation.
5) L-histidinol, an analogue of the L-histidine amino acid. Its action is through preferential prevention of the entry of normal cells into cell cycle (through protein deficiency), whereas malignant cells (permissive for protein starvation) continue to cycle (Edelstein (9)).

A second way is through using biological response modifiers that directly interact with the complex immunological and hematopoietic processes (immunomodulators).

This can be by either indirect interfering with synthesis of cytokines and/or hematopoietic growth-and/or inhibitory factors or by directly modulating the amount of these factors, which are nowadays available in recombinant form. Within this group of immunomodulators one can distinguish:

1) Endotoxin (LPS), that stimulate the cells of the reticulo endothelial system. Its pathophysiological effects are mediated by cytokines such as IL-1, TNF alfa, IL-6, CSF's and interferons (IFN's) (Ainsworth (10)).
2) The microbial agent glucan (Hofer et al. (11)), an immune and hemopoietic stimulant that enhances hematopoietic repopulation, which can be combined with the already mentioned sulfhydryl compounds or antiinflammatory compounds.
3) The immunomodulator AS101 that stimulates the production of various cytokines (ex. IL-1) (Kalechman et al. (12)).

4) A class of inhibitory peptides that inhibit hemopoietic stem cell proliferation:
   4a) pEEDCK or HP5b (Paukovits et al. (13)),
   4b) LtriP (Migliore-Samour et al. (14)),
   4c) AcSDKP (Bonnet et al. (15)).
5) Hematopoietic stimulatory and/or inhibitory growth factors or cytokines:
   5a) IL-1 (Eastgate et al. (16))
   5b) TNF-alfa (Warren et al. (17))
   The radioprotective effects of these two cytokines have been linked to the induction of the antioxidant enzyme MnSOD (Eastgate et al. (16)). TNFalfa also induces cell cycle arrest (Warren et al. (17)).
   5c) TGF-beta (Pierce and Coffey (18))
   5d) MIP-1-alfa (Eaves et al. (19))
   Both TGFbeta and MIP1alfa appear to have a differential effect on bone marrow progenitors depending on the maturation state: early progenitors are inhibited from cycling whereas later progenitors are being stimulated.
   5e) Il6 (Neta et al. (20))
   5f) KL (Zsebo et al. (21))
   5g) G- and/or GM-CSF (Grant et al. (22))
   These factors are no true stem cell protectors: they are administered to enhance regeneration and shorten the duration of blood aplasia.
   5h) BFGF (Gallicchio et al. (23))
   5i) Interferon inducible protein 10 (Sarris et al. (25))

Some reports showed suppressive effects of IFN-γ on commited progenitor cells (Zoumbos et al. (39), Broxmeyer et al. (40), Rigby et al. (41)). However, in these reports, various crude conditioned media were used to stimulate progenitor cell proliferation, the experiments were performed with relatively unpurified bone marrow populations and lastly single cell assays were never performed so that mostly indirect effects were probably measured.

From Richman et al. (24) it is known that interferon-γ protects normal human granulocyte/macrophage colony-forming cells (CFU-GM) in vitro from Ara-C cytotoxicity if these cells were treated with IFN-γ one hour before Ara-C exposure. The increase of survival of the cells is however not very significant (from 29+5% to 45+2%). Furtheron, CFU-GM are committed cells which are late progenitor cells and therefore no multipotential progenitors.

Finally, it is also noteworthy that in a clinical setting, it is preferred that bone marrow protecting agents should be selective in their action, i.e. they should protect especially stem cell preparations without protecting tumor tissue, or at least so at a lower degree.

SUMMARY OF THE INVENTION

In one aspect the invention herein concerns methods for the in vivo and in vitro inhibition of proliferation and differentiation of primitive hematopoietic cells and hematopoietic stem cells by incubating said cells with an effective amount of IFN-γ. The invention further comprises a method for chemoprotection and radioprotection of primitive hematopoietic cells and hematopoietic stem cells, preferably during culturing procedures using IFN-γ.

It is preferred to use interferon-γ as a protective agent in a range of concentration from about 100 to 10,000 U/ml for in vitro purging procedure and, at a dose of about 1,000,000 U/m$^2$ of body surface area (to be administered subcutaneously three times weekly before and during chemotherapy), for in vivo protective purposes. Patients with the following tumors would be candidates for adjuvant treatment with γ-interferon: non-Hodgkin's lymphoma, Hodgkin's lymphoma, multiple myeloma, testis carcinoma, breast cancer, soft tissue sarcomas, osteosarcomas, ovarium carcinoma, oat cell lung cancer and others.

The advantages offered by the method according to the invention especially are as follows:
1) IFN-γ is a selective inhibitor;
2) Its action is completely reversible;
3) IFN-γ maintains the viability of the cells it is inhibiting;
4) IFN-γ's pharmacokinetics and dynamics in humans are well known (e.g. use of IFN-γ in the management of chronic granulomateous disease (New England Journal of Medicine (53)), and e.g. in the treatment of refractory disseminated non-tuberculose mycobacterial infection (Holland et al. (54)); and finally
5) it has already been proven that IFN-γ has antitumoral effects in some instances.

DETAILED DESCRIPTION OF THE INVENTION

Figure 1:
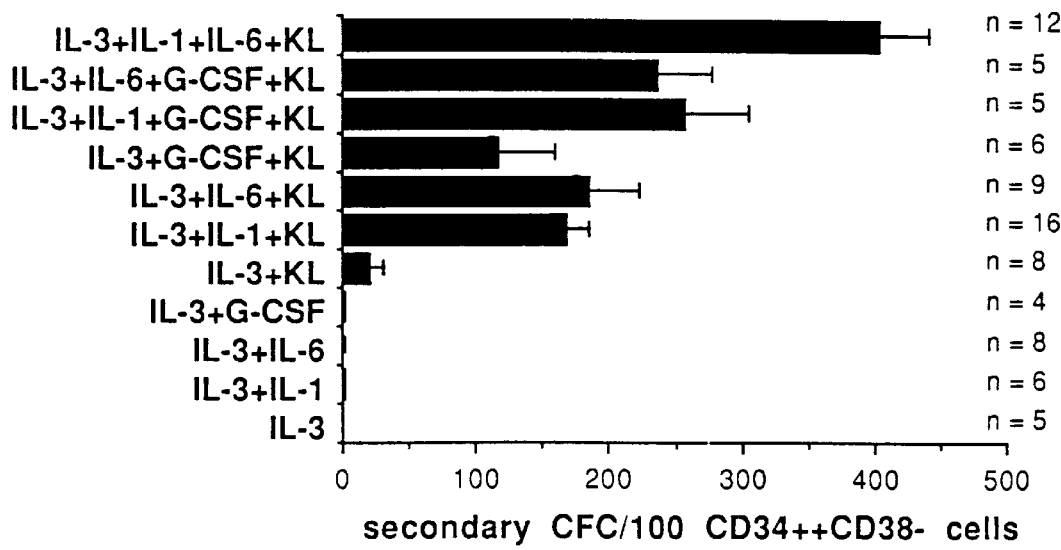
FIG. 1 Effect of primary culture of purified CD34++ CD38− bone marrow cells in the presence of the cytokine combinations mentioned on the Y-axis on the generation of secondary CFC. Results expressed as the number of secondary CFC per 100 CD34++CD38− cells (mean+standard error of the mean (SEM)). The number of independent experiments is indicated on the right hand side of the figure (n).

The invention provides a method for inhibition of proliferation of primitive hematopoietic progenitor cells and hematopoietic stem cells by incubating said cells with an effective amount of IFN-γ, in vivo and/or in vitro.

The effective amount depends on the amount of cells per ml which will be inhibited as well as on the cell culture medium and the type and amount of cytotoxic measures. Such cytotoxic measures are, for example, the addition of substances such as cytotoxic agents or the use of photoradiation. However, it is useful to employ IFN-γ at a concentration of 100 to 10,000 U/ml, preferably 500 to 5000 U/ml, or most preferably at a concentration of about 1000 U/ml (activity according to EMC-virus/L-cell standard system).

The doses of the cytotoxic or chemotherapeutic agent are those standardly used for the particular condition and agent. For instance, for the treatment of multiple myeloma: melphalan 140–200 mg/m².

the BEAM conditioning regimen, that is mainly used as a preparative treatment for autologous bone marrow transplantation in Hodgkin's lymphoma, and sometimes also in non-Hodgkin's lymphoma: BCNU 300 mg/m² on day 1; etoposide 200 mg/m²/day on days 2, 3, 4 and 5; ARA-C 200 mg/m² every 12 hours, on days 2, 3, 4 and 5; melphalan 140 mg/m² on day 6.

the CAV treatment schemes, used for small cell lung cancer (oat cell carcinoma): for instance doxorubicin 50 mg/m², cyclophosphamide 1000 mg/m² and vincristine 2 mg.

the VIP treatment scheme, that is used in Ewing sarcoma: etoposide 100 mg/m²/day for 3 days, ifosfamide 1000 mg/m²/day for 5 days, cisplatinum 20 mg/m²/day for 5 days, this treatment is sometimes alternated with the VAI scheme: vincristine 2 mg/day for 3 days, adrimycine 20 mg/m²/day for 3 days and ifosfamide 3 g/m²/day for 3 days. These schemes are non-limitative, and variations are within the scope of the present invention.

The effective amount depends on the applied concentration of primitive hematopoietic progenitor cells and hematopoietic stem cells and the applied purging method. It can, however, be detected easily by measuring how effective the hematoprotection of said cells is. Such methods are known in the state of the art; see, for example, Lemoli, R. M., Strife, A, Clarkson, D. B., Haley, J. D., Gulati, S.C.: TGF-beta 3 protects normal human hematopoietic progenitor cells treated with 4-hydroxycyclophosphamide in vitro, Exp. Hematol., 1992, 20:1252; and Grzegorzewski. K., Ruscetti, F. W., Usiu, N., Damia, G., Longo, D. L., Carlino, J. A., Keller, J. R., Wiltrout, R. H. Recombinant transforming growth factor $\beta_1$ and $\beta_2$ protect mice from acutely lethal doses of 5-fluorouracil and doxorubicin, J. Exp. Med., 1994, 180:1047, which are hereby incorporated by reference. For example, hematoprotection by IFN-γ could be evaluated by pre-incubating said cells with IFN-γ in combination with a chemotherapeutic drug (for instance, adriamycine), followed by a classical pre-CFU-assay (after washing away the drug and IFN-γ).

The protective effect of IFN-γ's action on primitive hematopoietic progenitor cells and hematopoietic stem cells is fully reversible. Therefore, after removing IFN-γ from said cells, said cells will proliferate and differentiate in vitro and in vivo under appropriate conditions.

The reversibility can be affirmed by removing IFN-γ assaying for early hematopoietic cells (i.e. pre-CFU-assay) and comparing the results to a control experiment (without adding IFN-γ).

The invention further provides a method of purging of a hematopoietic cell preparation, in vitro and/or in vivo (i.e. bone marrow or mobilized peripheral blood progenitor cells and/or stem cells) in order to remove clonogenic tumor cells characterized in that the purging is done during stimulation of the proliferation, and preferably also during differentiation, of said cells, preferably by cytokines and in the presence of an amount of IFN-γ which inhibits proliferation of primitive hematopoietic progenitor cells and hematopoietic stem cells to an extent of about 70%, preferably about 100%.

Such cytokines are, for example, IL-3, IL-1, IL-6, KL, EPO, G-CSF and/or GM-CSF.

Surprisingly, it was found that IFN-γ has, in addition, a stem cell survival-enhancing effect. It was found that after 4 days, in a culture of primitive hematopoietic progenitor cells and hematopoietic stem cells with IFN-γ 68 of 100 cells initially present survive. During the control experiment without any support of IFN-γ only 31 of 100 cells initially present survive.

One advantage of the IFN-γ treatment during purging under stimulation of cell proliferation is that only the very early stem cells (primitive hematopoietic progenitor cells and hematopoietic stem cells) survive. Committed progenitor cells as granulocyte/macrophage colony-forming cells (CFU-GM) die also to a considerable extent (preferably to an extent of at least about 70%, preferably 80%, or most preferably more than 90% or 95%).

Therefore, the purging method of the invention offers the advantage of providing a still more complete and more definite destruction of tumor cells (which might be at the stage of committed cells).

A further aspect of the invention is a method of purging of a hematopoietic cell preparation (i.e. bone marrow or mobilized peripheral blood progenitor cells and/or stem cells) in order to remove clonogenic tumor cells characterized in that the purging is done in the presence of high doses of cytotoxic agents which kill committed progenitor cells to a considerable extent (preferably to an extent of at least about 70%, preferably 80%, or most preferably more than 90%) and in the presence of an amount of IFN-γ which inhibits proliferation of primitive hematopoietic progenitor cells and hematopoietic stem cells to an extent of about 70%, preferably about 100%.

A further aspect of the invention is a method for increasing the survival of primitive hematopoietic progenitor cells and hematopoietic stem cells during cell culture, characterized in that the cell culture is carried out in the presence of IFN-γ.

A further aspect of the invention is a method of preparing a preparation of primitive hematopoietic progenitor cells and hematopoietic stem cells which is substantially free of clonogenic tumor cells, by purging using cytotoxic agents in the presence of IFN-γ in an amount which inhibits proliferation of primitive hematopoietic progenitor cells and hematopoietic stem cells during stimulation of the proliferation of said cells or in the presence of high doses of cytotoxic agents. Purging techniques are described in Areman et al. (51), which is incorporated herein by reference.

A further aspect of the invention is the use of IFN-γ for the manufacturing of a therapeutic agent for the inhibition of proliferation of primitive hematopoietic progenitor cells and hematopoietic stem cells during purging of hematopoietic cell preparation (i.e. bone marrow or mobilized peripheral blood progenitor cells and/or stem cells) and therefore protection primitive hematopoietic progenitor cells and hematopoietic stem cells said cells from cell death during stimulation of the proliferation of said cells or in the presence of high doses of cytotoxic agents.

A further aspect is the use of IFN-γ for in vivo administration to achieve protection of said cells against cytotoxic effects of chemotherapy for cancer.

A further aspect of the invention is the use of IFN-γ for the manufacture of a therapeutic agent for the prevention of exhaustion of the stem cell compartment during chemotherapeutic cytotoxic treatment. Chemotherapeutic treatment of human beings for tumor therapy is carried out in such fashion that the cytotoxic chemotherapeutic agents are applied in several cycles, with a 3 to 4 weeks' intermission in between those cycles. By this cytotoxic treatment, most of the progenitor cells are killed. Therefore, the stem cells proliferate and differentiate in the time between the cycles. As a consequence of this, after several chemotherapeutic cycles, an exhaustion of the stem cell compartment is observed in the patients. IFN-γ prevents such exhaustion if it is administered before, during and after a chemotherapeutic cycle. It is preferred to administer IFN-γ at least 3 to 24 hours before the first chemotherapeutic cycle, during the cycle, and preferably, up to 1 to 2 weeks after the cycle. If there is an intermission between the chemotherapeutic cycles of about about 3 to 4 weeks, this means that the patient is given IFN-γ up to half the time of the chemotherapy-free period.

The preferred dose is, as mentioned supra, about 1,000,000 U/m$^2$ of body surface area. It is also preferred to administer IFN-γ three times a week.

It is also preferred to use IFN-γ as a therapeutic agent in combination with cytokines, especially GM-CSF and G-CSF.

Primitive hematopoietic progenitor cells and hematopoietic stem cells (CD34++CD38− cells) are cells with high proliferative potential which are precursors of committed colony forming cells, the latter being assayed in classical clonogenic assays in semi solid medium (Pluznik and Sachs (55); Ichikawa et al. (49); Bradley and Metcalf (50)).

The inhibition of proliferation of CD34++CD38− cells by IFN-γ is, for example, measured in a suspension culture. The CD34++CD38− cells are grown with and without IFN-γ. After a week, the surviving cells are counted. An effective amount of IFN-γ inhibits at least 70%, preferably about 100%, of said cells in relation to the control without IFN-γ.

Primitive human hematopoietic progenitor cells and hematopoietic stem cells are characterized by a high expression of CD34 and the absence of CD38 expression (CD34++CD38− cells). Upon differentiation and lineage commitment, the expression of CD38 increases while the expression of CD34 decreases (CD34+CD38+ cells) (Terstappen et al. (33), Huang and Terstappen (34)). In order to study the effects of IFN-γ on the early stages of the development of these very primitive human progenitor cells we used a pre-colony-forming cell (pre-CFC) assay (Iscove et al. (35), Smith et al. (36)) where the effects of the presence of IFN-γ in primary cultures of CD34++CD38− cells on the output of secondary colony-forming cells (CFC) was studied. IFN-γ is a potent and selective direct inhibitor of CD34++CD38− and not of CD34+CD38+ cells. IFN-γ may play a role in protecting the stem cell compartment from exhaustion in situations of hematopoietic stress and could be useful for the specific protection of hematopoietic stem cells against chemotherapy for cancer. The terms "primitive hematopoietic progenitor cells and hematopoietic stem cells" and "CD34++CD38− cells" are used as synonyms in this application.

The assay used identifies very primitive precursors of CFC, since CD34++CD38− cells which do not form colonies in semisolid media are stimulated to differentiate in suspension culture into CFC. CD34++CD38− cells, which according to the data of the invention also contain precursors of HPP-CFC which are considered to be very early progenitors (Bradley and Hogson (37), McNiece et al. (38), are known to be amongst the most primitive hematopoietic precursors (Terstappen et al. (33), Huang and Terstappen (34)). The fact that in the secondary cultures mostly colonies containing macrophages were recovered might indicate that a less primitive cell is detected here. However, many authors have shown that HPP-CFC also consist of mostly large macrophage-like cells (Bradley and Hogson (37), McNiece et al. (38)). Moreover, Lu et al. (52) showed that colonies with a high replating capacity generated from primitive CD34+++ cord blood cells consisted mostly of large macrophage-like cells. The development of stem cells in these in vitro assays thus seems to be biased towards the macrophage lineage. Since this is a two stage culture system, this assay allows the characterization of the direct effects of IFN-γ on the early phases of the development of primitive progenitor cells (from pre-CFC to CFC), without interference of any effects of IFN-γ on the terminal stages of differentiation (from CFC to mature cell), on which IFN-γ has been shown to have stimulatory effects (Caux et al. (27), Kawano et al. (28), Snoeck et al. (29), Shiohara et al. (30), Murohashi and Hoang (31)).

Differentiation and proliferation of primitive hematopoietic progenitor cells is tightly regulated by colony-stimulating factors (CSF) and by cytokines which act in synergy with CSF to stimulate the development of progenitor cells into mature cells (Ogawa (26)). Recently several reports have demonstrated direct stimulatory effects of interferon-γ (IFN-γ) on hematopoietic progenitor cells in synergy with other hemoregulatory cytokines such as interleukin (IL)-3 (Caux et al. (27), Kawano et al. (28), Snoeck et al. (29)), granulocyte macrophage colony-stimulating factor (Caux et al. (27), Kawano et al. (28), Snoeck et al. (29)), c-kit ligand (KL) (Shiohara et al. (30)) and the combination of IL-3 and erythropoietin (epo) (Murohashi and Hoang (31)). Moreover, IFN-γ stimulates the expansion of progenitor cells induced by IL-3, IL-6, IL-1, epo and KL (Brugger et al. (32)) and the growth of acute myeloblastic leukemia cells supported by IL-3 (Murohashi and Hoang (31)). The growth of GCSF responsive granulocytic progenitors however is directly inhibited by IFN-γ (Snoeck et al. (29)).

The invention surprisingly identifies IFN-γ as a direct bidirectional regulator of hematopoiesis whose inhibitory effects display a very strong specificity for very primitive progenitor and stem cells, as is evidenced by the fact that IFN-γ directly inhibits the early stages of the proliferation and differentiation of very primitive CD34++CD38− cells, but has no inhibitory effect on CD34+CD38+ cells. The smaller decrease in secondary colony formation induced by IFN-γ in primary cultures of CD34++CD38− cells supported by IL-3+KL (FIG. 2A) might be interpreted in the same context, since the CD34++CD38− cells stimulated by this cytokine combination are probably less primitive than cells which require a combination of 3 or 4 cytokines in order to proliferate. These effects are moreover undoubtedly direct effects since they were also seen in single cell culture experiments.

A number of recent reports (Snoeck et al. (29)) demonstrate direct stimulatory effects of IFN-γ on human hematopoietic progenitor cells in synergy with IL-3 and GM-CSF (Caux et al. (27), Kawano et al. (28), Snoeck et al. (29)). Some reports even suggest that IFN-γ has a selective stimulatory effect on more primitive progenitors in the murine system (Shiohara et al. (30)). However, in these reports the effects of IFN-γ on progenitor cells responsive to single CSF was assessed, indicating that more mature progenitor cells were studied.

Surprisingly, according to the invention, IFN-γ does not inhibit, nor stimulate the proliferation and differentiation of more mature CD34+CD38+ population stimulated by IL-3, IL-1, IL-6 and KL and epo. The data of Brugger et al. (32) who showed that IFN-γ stimulates the expansion of CFC induced by the same four cytokine combination using peripheral blood CD34+ cells could not be confirmed for CD34++CD38− cells. Differences in target cell populations and purity, or in cell isolation procedure and culture could account for this discrepancy. Other cytokines which have been identified as negative regulators of hematopoiesis, i.e. TGB-β (Ohta et al. (42), Keller et al. (43), Sing et al. (44)) and some members of the chemokine-family of cytokines, amongst which MIP-1α (Graham et al. (45), Broxmeyer et al. (46), Broxmeyer et al. (47), tend to display a selectivity for the inhibition of primitive progenitor cells, but, in contrast to IFN-γ (Caux et al. (27), Kawano et al. (28), Snoeck et al. (29)), they also inhibit committed early human erythroid and myeloid progenitor cells responsive to single CSF or to combinations of two growth factors (Keller et al. (43), Sing et al. (44), Graham et al. (45), Broxmeyer et al. (46)). Amongst the more mature progenitor cells, only the G-CSF-induced proliferation of relatively mature progenitors committed to the neutrophilic lineage is directly inhibited by IFN-γ (Snoeck et al. (29)). Quite surprisingly, besides inhibiting the growth factor-induced proliferation of CD34+ +CD38− cells, IF-γ also maintains their viability in the absence of other cytokines. Such phenomenon has not been described for TGF-β and MIP-1α. It was already shown that IFN-γ promotes the survival of more mature human committed erythroid and myeloid progenitor cells (Snoeck et al. (48)). IFN-γ probably inhibits apoptosis of progenitor cells. However, due to the very limited number of CD34++CD38− cells which could be isolated from a bone marrow sample this mechanism could not be confirmed by either demonstrating a DNA-ladder or by flow cytometry.

Since IFN-γ is an inflammatory cytokine which at the same time inhibits proliferation and cell death of very primitive progenitor cells and stimulates proliferation of more mature progenitors, it might, in situations of increased demand for blood cells such as infection, inflammation and blood loss, stimulate the expansion of committed progenitor cells and their proliferation and differentiation into mature cells (Caux et al. (27), Kawano et al. (28), Snoeck et al. (29), Shiohara et al. (30), Murohashi and Hoang (31), Brugger et al. (32)), while at the same time sparing the cells of the very primitive stem cell compartment from recruitment and thus protecting this compartment from exhaustion. IFN-γ could therefore be useful in the setting of chemotherapy for cancer as a stem cell protecting agent against cell cycle specific drugs.

In a further aspect of the invention, there is provided a method for the preparation of a mixture of primitive hematopoietic progenitor cells and hematopoietic stem cells, which is substantially free from CD34+CD38+ hematopoietic progenitor cells, characterized in that a hematopoietic cell preparation (i.e. bone marrow or mobilized peripheral blood progenitor cells and/or stem cells) is subjected to cytotoxic treatment and primitive hematopoietic progenitor cells and hematopoietic stem cells are separated from the dead CD34+ CD38+ hematopoietic progenitor cells. The separation can be carried out according to the state of the art. For instance, there is applied a density gradient, a column with an anti-CD34 antibody, or a marker separation. Such a mixture is free of CD34+CD38+ cells to an extent of at least 60%, preferably 80%, or most preferably 90%. The preparation is especially useful for autologous or allogenic stem cell transplantation, because there is a high certainty that this preparation does not contain tumor cells.

In a preferred embodiment of the invention, the cell growth, the cytotoxic treatment and/or purging is done in the presence of cytokines such as IL-1, IL-3, IL-6, KL, G-CSF, GM-CSF and/or EPO.

The following examples are provided to aid in the understanding of the present invention, the true scope of which is set forth in the appended claims. It is understood that modifications can be made in the procedures set forth without departing from the spirit of the invention.

EXAMPLE 1

Isolation of Bone Marrow Cells

Bone marrow samples were aspirated by sternal puncture from hematologically normal patients undergoing cardiac surgery, after informed consent according to the regulations of the Ethics Committee of the University of Antwerp, in tubes containing 2 ml Iscove's Modified Dulbecco's Medium (IMDM, GIBCO, Paisley, UK) and 5 U/ml preservative free heparin (Novo Industries, Denmark). Cells were separated on a Lymphocyte Separation Medium (LSM, Boehringer Mannheim GmbH, Germany) density gradient and washed twice. Remaining RBC were lysed using an NH4Cl containing lysing solution.

EXAMPLE 2

Cytokines and Monoclonal Antibodies

AntiCD34 antibodies are produced according to U.S. Pat. Nos. 4,714,680; 4,965,204 and 5,035,994. FITC-conjugated rabbit anti-mouse immunoglobulin F(ab')2 fragments (RAM) were purchased from Dako (Glostrup, Denmark). Phycoerythrin (PE)- and PE-conjugated anti-CD38 (IgG1) antibodies as well as isotype specific control antibodies were purchased from Becton Dickinson (Erembodegem, Belgium). Monoclonal neutralising anti-IFN-γ (monoclonal anti-Interferon-antibody, human IgG, Catalogue No. 1296825) and irrelevant control antibody (an isotype-matched antibody, that recognizes an irrelevant epitope, which is the proper control for the relevant specific antibody, that recognizes the specific antigen) (monoclonal anti-digoxigenin antibody IgG, Catalogue No. 1333062) were obtained from Boehringer Mannheim GmbH, Germany. Recombinant human IFN-γ (specific activity 2.107 U/mg), IL-6 (108 U/mg) and IL-1 (5.107 U/mg) were also obtained from Boehringer Mannheim GmbH, Germany. Erythropoietin was purchased from Cilag (Brussels, Belgium, 105 U/mg).

EXAMPLE 3

Cell Sorting

Bone marrow cells were incubated at $10^7$ cells/ml with 43A1 supernatant in a 1/10 dilution for 20 min. at 4° C., washed twice in IMDM containing 2% FCS, incubated with fluoresceinated RAM (1/50 dilution) for 20 min. at 4° C. and washed twice again. After washing the cells twice in IMDM+2% FCS, they were sorted on a FACStarPLUS cell sorter (Becton Dickinson, Erembodegem, Belgium) equipped with an air cooled argon ion laser ILT model 5500A (Ion Laser Technology, Salt Lake City, Utah). Cells with a low to medium forward scatter and a low side scatter, a highly positive green (CD34) fluorescence and an orange (CD38) fluorescence signal lower than the mean fluorescence of cells labeled with control antibody+2 standard deviations were sorted using a FACStar Plus cell sorter (BDIS) equipped with an Argon-ion laser. Purities were always >95%.

EXAMPLE 4

Pre-CFU Assay

Primary liquid cultures were performed in 96-well flat bottom plates in duplicate at 100 cells/well in Iscove's Modified Dulbecco's Medium, 10% fetal calf serum and combinations of the following recombinant human cytokines: 100 ng/ml IL-1, 200 U/ml IL-6, 100 ng/ml G-CSF, 30 U ml/ml IL-3, 100 ng/ml KL and varying concentrations of IFN-γ. After 14 days of primary culture the number of cells in each well was counted using an inverted microscope at 250x magnification, after which the cells were harvested, washed three times in IMDM+10% FCS, and plated in secondary methylcellulose cultures (0.9%) supplemented with 20% FCS, 1% bovine serum albumin (BSA), 10–5M 2-mercaptoethanol, 30 U/ml IL-3, 100 ng/ml G-CSF, 100 ng/ml GM-CSF and 2 U/ml epo, which were optimal concentrations for colony formation in preliminary experiments. These cultures were microscopically scored for colony formation after 14 and after 21 days culture at 37 C. in 5% $O_2$ and 5% $CO_2$ in a fully humidified incubator.

In order to ascertain that the effects of IFN-γ in these experiments were direct, the same experiments were performed at a single cell level. CD34++CD38– cells were sorted at 1 cell per well in 96-well V-bottomed plates (2 plates per cytokine combination). In test sorts using fluorescent microbeads, on average less than 2% of the wells contained no beads and no wells were detected which contained more than 1 bead. Each well contained 100 l of culture medium consisting of IMDM, 10% FCS, IL-1, IL-6, IL-3 and KL (concentrations as in the primary cultures described in FIG. 1) and either no IFN-γ or IFN-γ at 1000 U/ml. After 14 days of culture (37° C., 5%, $CO_2$ in a fully humidified incubator), the number of wells where growth had occurred (primary colonies) was scored using an inverted microscope, the primary colonies were harvested, washed 4 times and were individually plated in secondary methylcellulose cultures as described above. Secondary colony formation was observed after 14 days and 21 days of secondary culture. Parallel experiments were performed using CD34+CD38+ cells (which constitute the remainder of the CD34+ cells).

In a number of experiments, the cells were first cultured in the presence or absence of IFN-γ without any other cytokines for 4 days in 96-well flat bottom plates, after which the number of remaining cells was counted by phase contrast microscopy (250xmagnification). Shrunken, dull appearing cells with a ruffled cell membrane were considered to be dead cells and were not counted. The cells were then harvested, washed and cultured in liquid culture medium for 14 days in the presence of KL (100 ng/ml), IL-1 (100 ng/ml), IL-6 (200 U/ml) and IL-3 (30 U/ml). After 14 days of culture the cells were harvested, washed and plated out in secondary methylcellulose cultures as described above. In all experiments, Student's t-test for paired samples was used.

EXAMPLE 5

Cytokine Requirements of CD34++CD38– Cells

Figure 2:
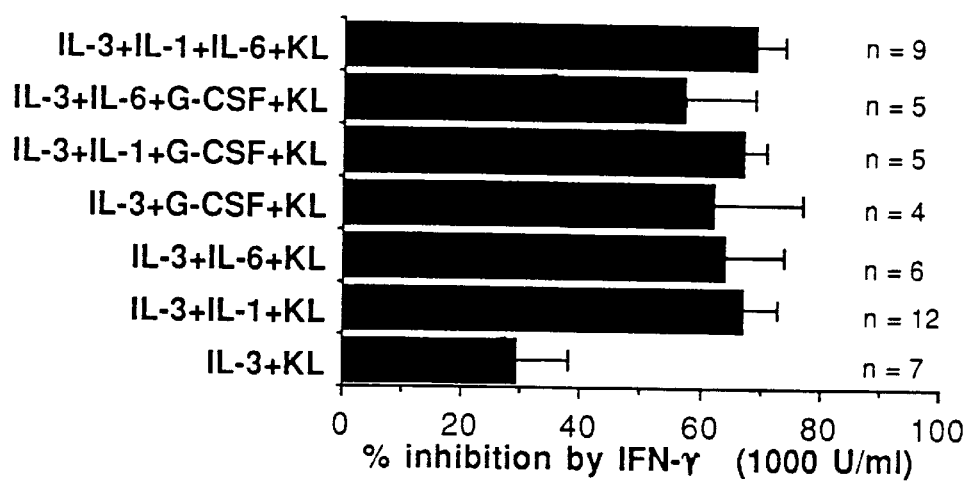
FIG. 2 Relative inhibition induced by IFN-γ (1000 U/ml) in the 14 day-primary liquid cultures of CD34++CD38− cells, supported by the cytokine combinations mentioned on the Y-axis, on the generation of secondary colonies (results expressed as mean+SEM). The number of independent experiments is indicated on the right hand side of the figure (n). The IFN-γ-induced inhibition was statistically significant in all cases ($p<0.05$, Student's t-test for paired samples).

The CD34++CD38– fraction comprises around 0.01 to 0.05% of human bone marrow cells and 1 to 5% of the CD34+ cells. These cells hardly form any colonies when plated directly in semisolid methylcellulose cultures in the presence of combinations of colony-stimulating factors (CSF) such as interleukin (IL)-3, granulocyte-macrophage-CSF (GM-CSF) and granulocyte-CSF (G-CSF) and erythropoietin (epo) (cloning efficiency less than 2%, results not shown). However, when cultured in primary liquid cultures for 14 days in the presence of combinations of multiple early acting factors (for a review, see (26)), the CD34++CD38– cells give rise to committed progenitor cells which do form colonies in secondary methylcellulose cultures (secondary colony-forming cells (CFC)). In order to generate secondary CFC, CD34++CD38– require at least the presence of IL-3, c-kit ligand (KL) and either IL-1, IL-6 or G-CSF in the primary liquid cultures (FIG. 1). No secondary CFC were generated in the absence of either IL-3 or KL (FIG. 1), and only few secondary CFC were produced in the presence of IL-3 and KL without any other synergistic factors in the primary liquid cultures (FIG. 1). The secondary colonies generated from CD34++CD38– cells were mostly myeloid with less than 2% of erythroid or mixed erythroid/myeloid colonies. Most of the myeloid colonies consisted of large macrophages. Addition of epo to the primary cultures had no effect on the number nor on the morphology of the secondary colonies. When the secondary cultures were scored at day 21 secondary high proliferative potential CFC (HPP-CFC, defined as macroscopic colonies of >2 mm diameter with a dense center, consisting mostly of large macrophage-like cells) were noted (FIG. 2). These HPP-CFC are believed to arise from more primitive progenitor cells than other colony types (Bradley and Hogson (37), McNiece et al. (38)).

EXAMPLE 6

Figure 3:
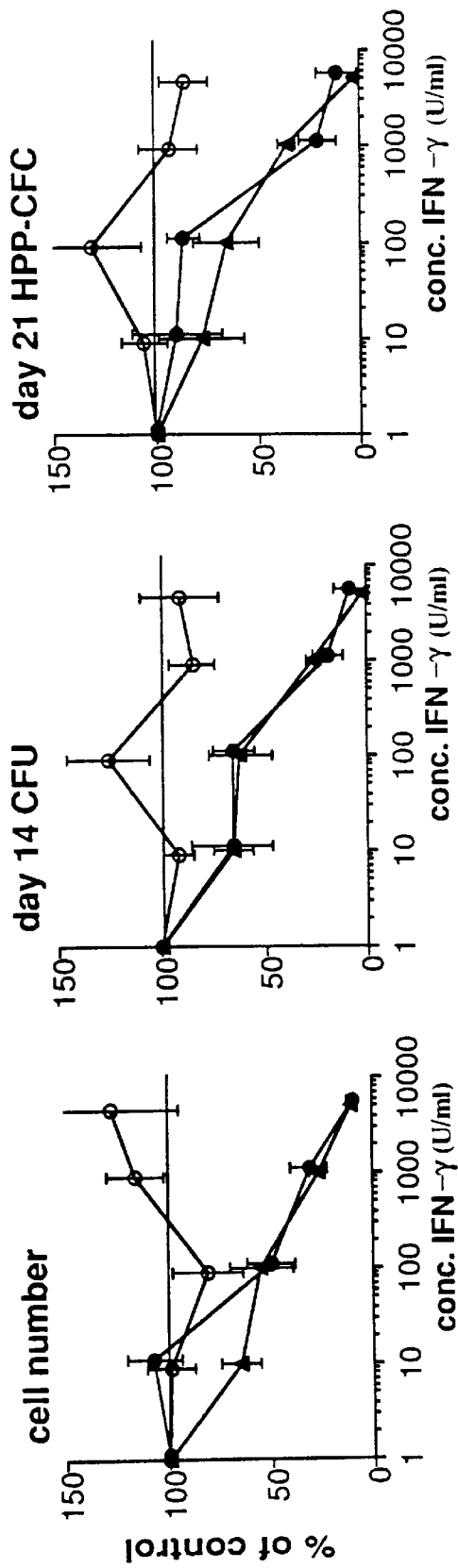
FIG. 3 Dose response curve of the effect of IFN-γ (Δ), IFN-γ+neutralising anti-IFN-γ antibody (O), and IFN-γ+ irrelevant control antibody (●) on the total primary liquid culture cell number (left), number of secondary day 14 CFC (middle) and secondary day 21 HPP-CFC (right) after 14 days of primary liquid culture of CD34++CD38− cells with IL-1, IL-6, IL-3 and KL. Results (mean+SEM) expressed percentage of inhibition, compared to primary cultures without IFN-γ. The number of cells after 14 days of primary culture without IFN-γ was 1318+354, the number of secondary day 14 CFC 473+64, and the number of secondary day 21 HPP-CFC was 61+10 per input of 100 CD34++ CD38− cells (pooled results of 5 independent experiments performed in duplicate).

Effects of IFN-γ on CD34++CD38– and CD34+ CD38+ Cells in Single Cell Culture a) IFN-γ inhibits the proliferation and differentiation of CD34++CD38– cells When IFN-γ was added to the primary liquid cultures of CD34++CD38– cells (100 cells per well) stimulated by cytokine combinations which induce proliferation of CD34++CD38– cells (see FIG. 1), cell proliferation, and generation of secondary CFC and of secondary HPP-CFC were profoundly inhibited in a dose dependent way, with near complete inhibition occurring at 5000 U/ml (FIGS. 2 and 3). The inhibitory effect of IFN-γ was less pronounced, but still statistically significant, in cultures stimulated by IL-3+KL (FIG. 2). The inhibitory effect of IFN-γ was blocked by adding neutralizing antibodies to human IFN-γ to the cultures (FIG. 3).

In order to see whether this inhibition was a direct effect of IFN-γ, primary liquid cultures were performed at a single cell level, by sorting CD34++CD38– cells at 1 cell per well in 96-well plates in the presence of IL-3, IL-1, IL-6 and KL with or without IFN-γ. The wells in which growth had occurred as assessed by microscopic evaluation (primary colonies) were picked up, washed and plated individually in methylcellulose cultures supplemented with IL-3, GM-CSF, G-CSF and epo. In these single cell culture experiments, the presence of IFN-γ in the primary cultures inhibited the total number of secondary CFC to the same extent as in experiments where CD34++CD38– cells were cultured at 100 cells per well (−67.5+13.7% vs. −69.1+4.3%, respectively, at a concentration of 1000 U/ml, n=4), demonstrating that the inhibitory effect of IFN-γ on the proliferation of CD34++ CD38– cells is a direct one. IFN-γ primarily inhibited the number of CD34++CD38– cells forming primary colonies (Table IA), while the number of secondary CFC per individual primary colony was inhibited to a lesser extent (Table IB).

TABLE I

Effects of IFN-γ on CD34++CD38− and CD34+CD38+ cells in single cell culture

A. Number of primary colonies per 100 cells in single cell liquid cultures supported by IL-1, IL-6, IL-3 and KL

|  | No. IFN-γ | IFN-γ $10^3$ U/ml[1] | mean D[2] | n[3] | p[4] |
|---|---|---|---|---|---|
| CD34++ CD38− | 25.4 ± 2.9 | 13.3 ± 2.7 | −48.4 ± 6.7% | 6 | 0.0008 |
| CD34+ CD38+ | 22.6 ± 3.1 | 22.0 ± 3.3 | +1.8 ± 8.0% | 6 | 0.83 |

B. Number of secondary CFC per primary colony

|  | No. IFN-γ− | IFN-γ+ $10^3$ U/ml[1] | mean D | n[3] | p[4] |
|---|---|---|---|---|---|
| CD34++ CD38− | 73.4 ± 13.1 | 53.0 ± 18.1 | −20.0 ± 5.3% | 4 | 0.033 |
| CD35+ CD38+ | 0.7 ± 0.4 | 0.2 ± 0.2 | −0.5 ± 0.4% | 6 | 0.31 |

[1]Concentration IFN-γ: 1000 U/ml-1
[2]Mean difference (D) expressed as relative difference in terms of percentage compared to cultures without IFN-γ.
[3]Number of independent experiments
[4]Statistics used: Student's t-test for paired samples.

b) IFN-γ does not inhibit more mature CD34+CD38+ cells.

The same single cell culture experiments were performed using CD34+CD38+ bone marrow cells, which constitute the remainder of CD34+ cells (Table I). Strikingly, only 6.7+2.5% of the primary colonies generated from this population in the presence of IL-3, IL-1, IL-6 and KL contained secondary CFC (compared to 95.3+2.4% for primary colonies derived from the CD34++CD38− population, p=0.0001), and we never observed more then 10 secondary CFC per individual primary colony derived from CD34+ CD38+ cells, nor did we observe any secondary HPP-CFC. This indicates that this culture system allows a very sharp functional distinction of very primitive CD34++CD38− cells from more mature CD34+CD38+ cells. In contrast to the effects of IFN-γ on CD34++CD38− cells, addition of IFN-γ to primary cultures of CD34+CD38+ cells had no effect on the number of primary colonies nor on the number of secondary CFC (Table I). Moreover, IFN- did not inhibit colony formation in single cell methylcellulose cultures of CD34+CD38+ cells supported by epo, IL-1, IL-6, KL and IL-3 (mean cloning efficiency 30.8+2.6% without and 27.5+3.2% with IFN-γ at 103 U/ml respectively, n=6, p=0.35). Taken together, these data indicate that IFN-γ acts as a highly selective and direct inhibitor of the proliferation and differentiation of very primitive CD34++CD38− cells and not of more mature CD34+CD38+ cells.

c) IFN-γ stimulates the survival of CD34++CD38− cells.

In order to see whether preincubation of CD34++CD38− cells in IFN-γ also affects their subsequent capacity to generate secondary CFC, CD34++CD38− cells where first cultured for 4 days either in culture medium (IMDM, 10% FCS) or in culture medium containing IFN-γ, after which the cells were washed and a pre-CFC assay was performed as described above. When after 4 days preculture in either medium without cytokines or medium containing IFN-γ (103 U/ml) the cells where washed and cultured for another 14 days in the presence of IL-3, KL, IL-6 and IL-1, significantly more secondary CFC were recovered from the cells which had been precultured for 4 days in the presence of IFN-γ than in the absence of IFN-γ (mean difference +117±26%, p=0.02, n=4). This effect is due to a survival enhancing effect of IFN-γ, since significantly more morphologically intact cells, as determined by counting the cells in the culture wells by phasecontrast microscopy at 250x magnification, were recovered after 4 days culture with IFN-γ then after 4 days culture in medium without cytokines (respectively 68.5±2.9% and 31±4.8% of the input cell number, p=0.0008, n=5, $10^3$ U/ml IFN-γ). Both the effect on cell number and on the capacity to generate secondary CFC reached a plateau at an IFN-γ concentration of 50 U/ml, i.e. at a 2 log lower concentration than the concentration at which complete inhibition of the proliferation and differentiation of pre-CFC was noted (see FIG. 2). These data show that IFN-γ promotes the survival of CD34++CD38− cells and that preincubation in IFN-γ does not inhibit their subsequent proliferative capacity.

EXAMPLE 7

Treatment of Buffy Coat Cells with 4-Hydroperoxycyclophosphamide (Purging) in the Presence of Interferon-γ

From a bone marrow preparation for autologous transplantation residual marrow tumor cells are purged. The purged marrow is then frozen and the patient is treated with marrow lethal chemotherapy with or without total body irradiation. The purged marrow is thawed and infused to rescue the patient from the chemotherapy.

Bone marrow is harvested and the buffy coat cells are prepared according E. M. Areman et al. (51).

The treatment of buffy coat cells with 4-HC is also carried out according to Areman et al. (51), except for the addition of, and preincubation with, IFN-γ.

The buffy coat cell preparation is placed in a 37° C. water bath for 1 hour after the addition of IFN-γ at 1000 U/ml final concentration before the addition of 4-HC. 4-HC (200 mg vial) is reconstituted in 20 ml of room temperature Tc-199 media (Gibco 320-1151). This results in a solution containing 10 mg 4-HC/ml.

An appropriate amount of dissolved 4-HC (for details see Areman et al. (51), page 236–239) is added in an incubation bag through a 0.22 m filter attached to a syringe. After a 30-minute incubation the cells are transferred to 600 ml bags. The bags are centrifuged at 4° C. for 10 minutes as 2900 rpm and placed in the plasma expresser. As much media as possible is removed without losing cells. The graft is finally frozen by standard procedures.

REFERENCES

1) Selig C., Nothdurft W., Fliedner T. M., J. Cancer Res. Clin. Oncol. 119(6) (1993) 346–349

2) Vacek A., Rotkovska D., Bartonickova A., Kautska J., Folia. Biol. Praha 38(6) (1992) 323–331

3) Kozubik A., Pospisil M., Netikova J., Strahlenther. Onkol. 167(3) (1991 Mar) 186–190

4) Capizzi R. L., Scheffler B. J., Schein P. S., Cancer 72 (1993) (11 Suppl) 3495–3501

5) Hanson W. R., Ainsworth E. J., Radiat. Res. 103(2) (1985) 196–203

6) Walden T. L., Radiat. Res. 132 (1992) 359–367

7) Ramakrishnan N., Wolfe W. W., Catravas G. N., Radiat. Res. 130(3) (1992) 360–365

8) Floersheim G. L., Radiat. Res. 133(1) (1993) 80–87

9) Edelstein M. B., J. Natl. Cancer Inst. 81(4) (1989) 298–301
10) Ainsworth E. J., Pharmacol. Ther. 39(1–3) (1988) 223–241
11) Hofer M., Pospisil M., Viklicka S., Vacek A., Pipalova I., Bartonickova A., J. Leukoc. Biol. 53(2) (1993) 185–189
12) Kalechman Y., Shani A., Albeck M., Sotnik Barkai I., Sredni B., Radiat. Res. 136(2) (1993) 197–204
13) Paukovits W. R., Moser M. H., Paukovits J. B., Blood 81(7) (1993) 1755–1761
14) Migliore-Samour D., Bousseau A., Caillaud J. M., Naussac A., Sedqi M., Ferrradini C., Jolles P., Experentia 49(2) (1993) 160–166
15) Bonnet D., Cesaire R., Lemoine F., Aoudjhane M., Najman A., Guigon M., Exp. Hematol. 20(2) (1992) 251–255
16) Eastgate J., Moreb J., Nick H. S., Suzuki K., Taniguchi N., Zucali J. R., Blood 81(3) (1993) 639–646
17) Warren D. J., Slordal L., Moore M. A., Eur. J. Hematol. 45(3) (1990) 158–163
18) Pierce D. F. Jr., Coffey R. J., Am. Surg. 60(1) (1994) 18–25
19) Eaves C. J., Cashman J. D., Wolpe S. D., Eaves A. C., Proc. Natl. Acad. Sci. USA 90(24) (1993) 12015–12019
20) Neta R., Perlstein R., Vogel S. N., Ledney G. D., Abrams J., J. Exp. Med. 175(3) (1992) 689–694
21) Zsebo K. M., Smith K. A., Hartley C. A., Greenblatt M., Cooke K., Rich W., McNiece I. K., Proc. Natl. Acad. Sci. USA 89(20) (1992) 9464–9468
22) Grant S., Pettit G. R., McCrady C., Exp. Hematol. 20(1) (1992) 34–42
23) Gallicchio V. S., Hughes N. K., Hulette B. C., DellaPuca R., Noblitt L., Int. J. Cell Cloning 9(3) (1991) 220–232
24) Richman C. M., Slapak C. A., Toh B., J. Biol. Response Mod. 9(6) (1990) 570–575
25) Sarris A. H., Broxmeyer H. E., Wirthmueller U., Karasavvas N., Cooper S., Lu L., Krueger J., Ravetch J. V., J. Exp. Med. 178(3) (1993) 1127–1132
26) Ogawa M., Blood 81 (1993) 2844
27) Caux C., Moreau I., Sealand S., Banchereau J., Blood 79 (1992) 2628
28) Kawano Y., Takaue Y., Hirao A., Abe T., Saito S., Matsunaga K., Watanabe T., Hirose M., Ninomiya T., Kuroda Y., Yokobayashi A., Asano S., Blood 77 (1991) 2118
29) Snoeck H.-W., Lardon F., Nys G., Lenjou M., van Bockstaele D. R., Peetermans M. E., Eur. J. Immunol. 23 (1993) 1072
30) Shiohara M., Koike K., Nakahata T., Blood 81 (1993) 1435
31) Murohashi I., Hoang T., Blood 78 (1991) 1085
32) Brugger W., Möcklin W., Heimfeld S., Berenson R. J., Mertelsman R., Kanz L., Blood 81 (1993) 2579
33) Terstappen L. W. M. M., Huang S., Safford M., Lansdorp P., Loken M., Blood 77 (1991) 1218
34) Huang S., Terstappen L. W. M. M., Nature 360 (1992) 745
35) Iscove N. N., Shaw A. R., Keller G., J. Immunol. 142 (1989) 2332
36) Smith C., Gasparetto C., Collins N., Gillio N., Muench M. O., O'Reilly R. J., Moore M. A. S., Blood 77 (1991) 2122
37) Bradley T. R., Hogson G. S., Blood 54 (1979) 1446
38) McNiece I. K., Stewart F. M., Deacon D. M., Temeles D. S., Zsebo K. M., Clarke S. C., Queenberry P. J., Blood 74 (1989) 609
39) Zoumbos N., Djeu J. Y., Young N. S., J. Immunol. 133 (1984) 769
40) Broxmeyer H. E., Lu L., Platzer E., Feit C., Juliano L., Rubin B. Y., J. Immunol. 131 (1983) 1300
41) Rigby W. F. C., Ball E. D., McGuire P. M., Fanger M. W., Blood 65 (1985) 858
42) Ohta M., Greenberger J. S., Anklesaria P., Bassols A., Massagué J., Nature 329 (1987) 539
43) Keller J. R., Mantel C., Sing G. K., Ellingsworth L. R., Ruscetti S. K., Ruscetti F. W., J. Exp. Med. 168 (1989) 737
44) Sing G. K., Keller J. R., Ellingsworth L. R., Ruscetti F. W., Blood 72 (1988) 1504
45) Graham G. J., Wright E. G., Hewick R., Wolpe S. D., Wilke N. M., Donaldson D., Lorimore S., Pragnell I. B., Nature 344 (1990) 442
46) Broxmeyer H. E., Sherry B., Lu L., Cooper S., Oh O., Tekamp-Olson P., Kwon B. S:, Cerami A., Blood 76 (1990) 1110
47) Broxmeyer H. E., Sherry B., Lu L., Maze R., Beckmann M. P., Cerami A., Ralph P., J. Immunol. 150 (1993) 3448
48) Snoeck H. W., Lardon F., Nys G., Lenjou M., van Bockstaele D. R., Peetermans M. E., Exp. Hematol. 21 (1993) 1480
49) Ichikawa Y. et al., Proc. Natl. Acad. Sci. USA 56 (1966) 488–495
50) Bradley T. R. and D. Metcalf, Australian Journal of Exp. Biology and Medical Science 44 (1966) 287–300
51) Areman E. M. et al., Bone Marrow and Stem Cell Processing: A Manual of Current Techniques, F. A. Davies Co., Philadelphia (1992)
52) Lu L., Shen R., Grigsby S., Broxmeyer H. E., Blood 81 (1993) 41
53) New England Journal of Medicine 324 (1991) 509–516
54) Holland S. M., New England Journal of Medicine 330, 1348–1355
55) Pluznik D. H. and L. Sachs, J. of Cellular and Comparative Physiology 66 (1965) 319–324

We claim:

1. A method of promoting survival of hematopoietic cells among a population of hematopoietic and tumor cells, comprising contacting said population of cells with an effective amount of at least one agent for purging tumor cells in the presence of an effective amount of IFN-gamma sufficient to inhibit proliferation of CD34++CD38– cells, and removing IFN-gamma to reverse inhibition of proliferation.

2. A method according to claim 1, wherein said agent for purging tumor cells comprises at least one cytotoxic agent.

3. A method according to claim 1, where said agent comprises irradiation.

4. A method according to claim 1, further comprising contacting said population with at least one stimulating agent to promote proliferation of said tumor cells.

5. A method according to claim 1, further comprising contacting said cells with a cytokine other than IFN-gamma.

6. A method according to claim 1, wherein said agent for purging tumor cells is present in amounts sufficient to kill committed progenitor cells in said cell population.

7. A method according to claim 6, wherein said committed progenitor cells are CD34+CD38+ cells.

8. A method according to claim 1, further comprising the step of separating said hematopoietic cells from tumor cells killed by said agent for purging tumor cells.

9. A method according to claim 1, wherein said hematopoietic cells among said population of cells comprise bone marrow cells, mobilized peripheral blood progenitor cells and stem cells.

10. A method for separating tumor cells from bone marrow cells, comprising
   (a) obtaining bone marrow cells comprising a population of CD34++CD38− cells and tumor cells,
   (b) contacting said population with IFN-gamma in an amount sufficient to inhibit proliferation of said CD34++CD38− cells,
   (c) contacting said population with a cytotoxic agent to kill at least said tumor cells, and
   (d) thereafter removing cells killed by said cytotoxic agent and removing IFN-gamma from said population.

11. A method according to claim 10, wherein said cytotoxic agent is present in amounts sufficient to kill CD34+CD38+ cells.

12. A method for separating CD34++CD8− cells from CD34+CD38+ cells in vitro, comprising:
   (a) contacting a population of hematopoietic cells with (I) at least one cytotoxic agent to obtain dead CD34+CD38+ cells and (ii) IFN-gamma to inhibit CD34++CD38− cells, and
   (b) separating CD34++CD38− cells from the dead CD34+CD38+ cells.

13. A method according to claim 12 wherein the hematopoietic cell population is selected from the group consisting of bone marrow, mobilized peripheral blood progenitor cells and stem cells.

14. A method for preventing stem cell compartment exhaustion in a patient receiving chemotherapy, comprising administering to the patient an effective amount of IFN-gamma at a plurality of times comprising at least 3 to 24 hours before a chemotherapeutic cycle, during the cycle and after the cycle for at least 1 week.

15. The method of claim 14, wherein at least one cytokine is administered additionally.

* * * * *